United States Patent [19]

Howard, Jr. et al.

[11] Patent Number: 4,960,785

[45] Date of Patent: Oct. 2, 1990

[54] INDOLINONE DERIVATIVES

[75] Inventors: Harry R. Howard, Jr., Bristol; Reinhard Sarges, Mystic, both of Conn.

[73] Assignee: Pfizer Inc., New York, N.Y.

[21] Appl. No.: 346,115

[22] PCT Filed: Jun. 10, 1986

[86] PCT No.: PCT/US86/01429

§ 371 Date: Dec. 16, 1988

§ 102(e) Date: Dec. 16, 1988

[51] Int. Cl.$^5$ .................. C07D 209/34; C07D 209/96; C07D 491/056; A61K 31/40

[52] U.S. Cl. ..................... 514/411; 514/414; 514/418; 514/866; 548/431; 548/468; 548/486

[58] Field of Search ............. 548/431, 486, 468; 514/414, 411, 418

[56] References Cited

U.S. PATENT DOCUMENTS 3,821,383  6/1974  Sestanj et al. ............... 424/258
4,053,613  10/1977  Rovnyak ....................... 514/370
4,209,527  6/1980  Sarges ........................ 424/273

OTHER PUBLICATIONS

Howard et al., Chem. Abs 109, 6408e.

*Primary Examiner*—Mark L. Berch
*Attorney, Agent, or Firm*—Peter C. Richardson; Paul H. Ginsburg

[57] ABSTRACT

A series of novel 3-mono(substituted methyl)- and 3,3-di(substituted methyl)-2-oxo-indoline-1-alkanoic acid compounds have been prepared, including their lower alkyl esters and unsubstituted amide derivatives, as well as the base salts of said acids with pharmacologically acceptable cations. These compounds are useful in therapy as aldose reductase inhibitors for the control of certain chronic diabetic complications. Said oxindole-1-alkanoic acid compounds are of the formulae:

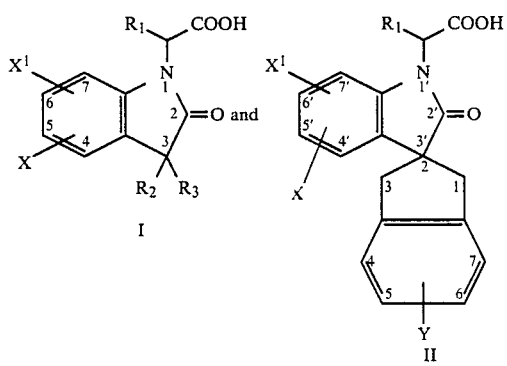

wherein X is hydrogen and $X^1$ is hydrogen, hydroxy, fluorine, chlorine, bromine, $C_1$–$C_4$ alkyl or $C_1$–$C_4$ alkoxy; or X and $X^1$, when taken separately, are each chlorine, $C_1$–$C_4$ alkyl or $C_1$–$C_4$ alkoxy, and when taken together are —OCH$_2$(CH$_2$)$_n$O— at the 4,5-, 5,6- or 6,7-positions of the molecule wherein n is zero or one; $R_1$ is hydrogen or methyl; $R_2$ is hydrogen, $C_1$–$C_4$ alkyl or phenylalkyl having up to three carbon atoms in the alkyl moiety wherein said phenylalkyl is optionally substituted with up to two chlorine substituents on the phenyl ring; $R_3$ is naphthylmethyl, furfuryl, thenyl, benzothienylmethyl, benzoxazolylmethyl, benzothiazolylmethyl or phenylalkyl having up to three carbon atoms in the alkyl moiety wherein said phenylalkyl is optionally substituted with up to two identical or non-identical substituents on the phenyl ring, said identical substituents being fluorine, chlorine, bromine, trifluoromethyl, $C_1$–$C_4$ alkyl or $C_1$–$C_4$ alkoxy and said non-identical substituents being chlorine, methyl, methoxy or trifluoromethyl; and Y is hydrogen, fluorine, chlorine, $C_1$–$C_4$ alkyl or $C_1$–$C_4$-alkoxy.

26 Claims, No Drawings

INDOLINONE DERIVATIVES

TECHNICAL FIELD

This invention relates to new indolinone derivatives of interest to those in the field of medicinal chemistry and chemotherapy. More particularly, it is concerned with a novel series of oxindole-1-alkanoic acid compounds for the control of certain chronic complications arising from diabetes mellitus (e.g., diabetic cataracts, retinopathy and neuropathy).

BACKGROUND ART

Past attempts to obtain new and better oral antidiabetic agents have, for the most part, involved an endeavor to synthesize new compounds that lower blood sugar levels. More recently, several studies have been conducted concerning the effect of various organic compounds in preventing or arresting certain chronic complications of diabetes, such as diabetic cataracts, neuropathy and retinopathy, etc. For instance, K. Sestanj et al. in U.S. Pat. No. 3,821,383 discloses that certain aldose reductase inhibitors like 1,3-dioxo-1H-benz[d,e]isoquinoline-2(3H)-acetic acid and some closely-related derivatives thereof are useful for these purposes even though they are not known to be hypoglycemic. These compounds function by inhibiting the activity of the enzyme aldose reductase, which is primarily responsible for catalyzing the reduction of aldoses (like glucose and galactose) to the corresponding polyols (such as sorbitol and galactitol) in the human body. In this way, unwanted accumulations of galactitol in the lens of galactosemic subjects and of sorbitol in the lens, retina, peripheral nervous system and kidney of diabetic subjects are prevented or reduced. As a result, these compounds control certain chronic diabetic complications, including those of an ocular nature, since it is already known in the art that the presence of polyols in the lens of the eye leads to cataract formation and concomitant loss of lens clarity.

DISCLOSURE OF THE INVENTION

The present invention relates to novel oxindole-1-alkanoic acid compounds useful as aldose reductase inhibitors for the control of certain chronic complications arising in a diabetic subject. More specifically, the novel compounds of this invention are selected from the group consisting of 3-substituted 2-oxo-indoline-1-alkanoic acids of the formula:

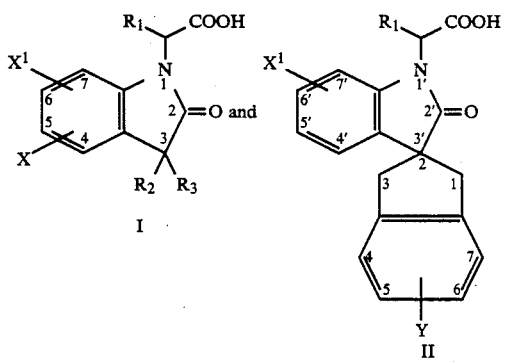

and the $C_1$–$C_6$ alkyl esters and primary amide derivatives thereof, and the base salts of said acids with pharmacologically acceptable cations, wherein X is hydrogen and $X^1$ is hydrogen, hydroxy, fluorine, chlorine, bromine, $C_1$–$C_4$ alkyl or $C_1$–$C_4$ alkoxy; or X and $X^1$, when taken separately, are each chlorine, $C_1$–$C_4$ alkyl or $C_1$–$C_4$ alkoxy, and when taken together are —$OCH_2(CH_2)_nO$— at the 4,5-, 5,6- or 6,7-positions of the molecule wherein n is zero or one; $R_1$ is hydrogen or methyl; $R_2$ is hydrogen, $C_1$–$C_4$ alkyl or phenylalkyl having up to three carbon atoms in the alkyl moiety wherein said phenylalkyl is optionally substituted with up to two chlorine substituents on the phenyl ring; $R_3$ is naphthylmethyl, furfuryl, thenyl, benzothienylmethyl, benzoxazolylmethyl, benzothiazolylmethyl or phenylalkyl having up to three carbon atoms in the alkyl moiety wherein said phenylalkyl is optionally substituted with up to two identical or non-identical substituents on the phenyl ring, said identical substituents being fluorine, chlorine, bromine, trifluoromethyl, $C_1$–$C_4$ alkyl or $C_1$–$C_4$ alkoxy and said non-identical substituents being chlorine, methyl, methoxy or trifluoromethyl; and Y is hydrogen, fluorine, chlorine, $C_1$–$C_4$ alkyl or $C_1$–$C_4$ alkoxy. These novel compounds are aldose reductase inhibitors and therefore, possess the ability to reduce or inhibit sorbitol formation in the lens and peripheral nerves of diabetic subjects.

One group of compounds of the present invention of interest is that of formula I wherein X is hydrogen; $X^1$ is hydrogen, hydroxy, fluorine, chlorine or $C_1$–$C_4$ alkoxy; X and $X^1$, when taken separately, are each $C_1$–$C_4$ alkoxy; $R_1$ is hydrogen or methyl; $R_2$ is hydrogen, $C_1$–$C_4$ alkyl or phenylalkyl having up to three carbon atoms in the alkyl moiety wherein said phenylalkyl is ring-substituted with up to two chlorine substituents on the phenyl ring; and $R_3$ is phenylalkyl as just hereinbefore defined for $R_2$. Preferred compounds within this group include those where X is hydrogen, $X^1$ is hydrogen, hydroxy, chlorine or methoxy, $R_1$ and $R_2$ are each hydrogen and $R_3$ is 3,4-dichlorobenzyl or 3,4-di-chloro-α-methylbenzyl.

Another group of compounds of the present invention of interest is that of formula II wherein X is hydrogen; $X^1$ is hydrogen, hydroxy, chlorine or methoxy; $R_1$ is hydrogen and Y is hydrogen, hydroxy, chlorine or methoxy. Preferred compounds within this group include those where X, $X^1$ and $R_1$ are each hydrogen and Y is hydrogen or chlorine at the 5(6)-position of the molecule.

Of special interest are such typical and preferred member compounds of the invention as 3-(3,4-dichlorobenzyl)-2-oxo-indoline-1-acetic acid, 5-chloro-3-(3,4-dichlorobenzyl)-2-oxo-indoline-1-acetic acid, 3-(3,4-dichlorobenzyl)-6-methoxy-2-oxo-indoline-1-acetic acid, 3-(3,4-dichlorobenzyl)-6-hydroxy-2-oxo-indoline-1-acetic acid and 3-(3,4-dichloro-α-methylbenzyl)-2-oxo-indoline-1-acetic acid. These particular compounds are highly potent aldose reductase inhibitors.

DETAILED DESCRIPTION

In accordance with the process employed for preparing the novel compounds of this invention, an appropriately substituted 2-oxo-indoline-1-alkanoic acid aralkyl ester of the formula:

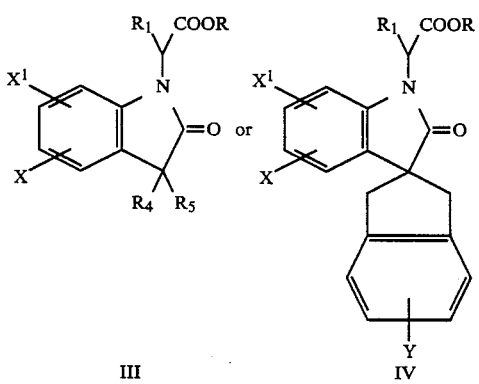

X, $X^1$, Y and $R_1$ are all as previously defined, R is an aralkyl group such as benzyl or a similar blocking group such as m-xylyl of p-chlorobenzhydryl and the like, $R_4$ and $R_5$ are each as previously defined for $R_2$ and $R_3$ except that $R_4$ is always other than hydrogen, or $R_4$ and $R_5$, when taken together, form the divalent groups $=R_6$ where $R_6$ is naphthylidene, furfurylidene, thenylidene, benzothienylmethylidene, benzoxazolylmethylidene, benzothiazolylmethylidene or phenylalkylidene having up to three carbon atoms in the alkylidene moiety wherein said phenylalkylidene is optionally substituted with up to two identical or non-identical substituents on the phenyl ring, said identical substituents being fluorine, chlorine, bromine, trifluoromethyl, $C_1$-$C_4$ alkyl or $C_1$-$C_4$ alkoxy and said non-identical substituents being chlorine, methyl, methoxy or trifluoromethyl, is subjected to the action of hydrogen in the presence of a noble metal catalyst until the reduction to form the desired final product is substantially complete. This hydrogenolysis reaction is normally conducted in a reaction-inert organic solvent at a pressure ranging from about 15 to about 50 p.s.i.g. and at a temperature that is in the range of from about 0° C. up to about 50° C. and preferably from about 15° C. to about 35° C. Preferred reaction-inert organic solvents for use in this connection include lower alkanols such as methanol, ethanol and isopropanol, lower dialkyl ethers such as diethyl ether, diisopropyl ether and di-n-butyl ether, as well as lower alkyl esters of lower alkanoic acids such as methyl acetate, ethyl acetate, isopropyl acetate, methyl propionate and ethyl propionate. The organic solvent will preferably contain a minor amount (e.g. 10-30% by weight) of an acid, which is usually an organic acid like glacial acetic acid or a similar lower alkanoic acid, but it can also be a substantially anhydrous mineral acid like phosphoric acid or sulfuric acid. Noble metal catalysts as employed herein include platinum, palladium, rhenium, rhodium and ruthenium, either of the supported or non-supported type, as well as the known catalytic compounds thereof, such as the oxides and chlorides, etc. The catalyst may be pre-formed or else formed in situ by the pre-reduction of an appropriate salt or oxide of the catalytic compound. Preferred catalysts for use in the reaction include platinum oxide and even more especially, palladium-on-carbon. Upon completion of the hydrogenolysis step, the desired oxindole-1-alkanoic acid final product is readily recovered from the resulting reaction mixture, viz., by first removing the catalyst from the reaction mixture by means of filtration and then concentrating the resulting filtrate to an oil or foam by means of evaporation under reduced pressure, followed by recrystallization from a suitable solvent system.

Compounds of the invention wherein $X^1$ of structural formulae I and II is hydroxy can be readily prepared from the corresponding compounds where $X^1$ is methoxy by simply dealkylating same in accordance with standard techniques well known to those skilled in the art. For instance, the use of boron tribromide in this connection readily converts 3-(3,4-dichlorobenzyl)-6-methoxy-2-oxo-indoline-1-acetic acid to the corresponding 6-hydroxy compound. Moreover, certain compounds of the invention (of structural formulae I-II) having a ring substituent ($X^1$) which is lower alkoxy of more than one carbon atom can alternatively be prepared from the corresponding methoxy compounds by first converting same to the corresponding hydroxy derivatives and then alkylating the latter with, for example, ethyl iodide or isopropyl bromide in a manner well known to those skilled in the art. As previously indicated, the oxindole-1-alkanoic acid final products (of structural formulae I-II) can be used as such for the therapeutic purposes of this invention or else simply converted to the corresponding lower alkyl ester and primary amide derivatives thereof in accordance with conventional techniques.

The lower alkyl esters of the 3-substituted 2-oxo-indole-1-alkanoic acids of this invention are generally prepared by condensation of the acid with the appropriate alcohol in the presence of an acid catalyst in accordance with conventional organic procedure. The primary amide derivatives are readily prepared, for example, by treating the corresponding acid chloride with ammonia under basic conditions and thereafter isolating the amide final product.

The aralkyl ester starting materials (of structural formulae III-IV) required for preparing the 3-substituted 2-oxo-indoline-1-alkanoic acid compounds of this invention, are all new compounds, which are prepared by treating the corresponding 3-substituted 2-indolinone (having a free hydrogen atom at the 1-position) with an appropriate α-haloalkanoic acid aralkyl ester of choice having the formula $ZCH(R_1)COOR$, where R and $R_1$ are each as previously defined in the structural formulae for the aralkyl esters and Z is either chlorine, bromine or iodine. This particular reaction is normally carried out in the presence of a basic condensing agent such as an alkali metal hydride, alkanolate or amide, or an alkali metal-alkyl or aryl compound, as the case may be, and is usually conducted in a reaction-inert polar organic solvent, preferably using one of the N,N-di(lower alkyl)lower alkanoamides. Preferred solvents in this connection include N,N-dimethylformamide, N,N-diethylformamide, N,N-di(n-propyl)formamide, N,N-dimethylacetamide, N,N-diethylacetamide, N,N-dimethylpropionamide and the like. In general, substantially equimolar amounts of reactant and reagent are employed (i.e., from about 0.80 to about 1.25 mole of halide reagent with respect to the 3-substituted 2-indolinone starting material) and the reaction is effected at a temperature that is in the range of from about 5° C. up to about 35° C. for a period of about 15 minutes up to about two hours. The reaction is usually conducted at room temperature for a period of time that is ordinarily less than about one hour. The basic condensing agents required for the reaction are all selected from the class of alkali metal bases previously enumerated which are sufficiently strong to form salts with the weakly acidic 3-substituted 2-indolinones and yet mild enough not to degrade the organic molecule under the conditions of the reaction. Such basic condensing agents include, for example, sodium hydride, lithium hydride and potassium hydride, etc., as well as sodium and potassium lower alkanolates like sodium methylate and potassium tert.-butoxide, as well as alkali metal amides like sodamide, lithium amide, potassium amide and so on. Upon completion of the reaction, the desired 3-substituted 2-oxo-indoline-1-alkanoic acid aralkyl esters are readily recovered from the reaction mixture by the use of standard techniques well-known to those skilled in the art, e.g., the reaction mixture may be first diluted with water and then extracted with a suitable solvent such as methylene chloride or chloroform, etc , to ultimately afford the desired intermediate esters after first removing the solvent from the organic extract.

The 3-substituted 2-indolinone compounds that are employed as starting materials in the above described reaction are all new compounds which are prepared by a number of different methods. For instance, 3-substituted 2-indolinone compounds where the 3-substituent is the divalent group $=R_6$ are prepared by condensing the corresponding 2-indolinone compounds with the appropriately-substituted aromatic or heteroaromatic aldehyde or ketone, such as 3,4-dichlorobenzaldehyde or 3,4-dichloroacet phenone, in a base-catalyzed manner to form the desired condensation product in accordance with the conventional methods of organic synthesis. This particular reaction is hereinafter described in some detail in the experimental section of the specification (see Preparations A-F). On the other hand, 3-substituted 2-indolinones where the 3-substituent is the disubstituted grouping $R_4$ and $R_5$, as previously defined for structural formula III and particularly where said disubstitution is symmetrical at the 3,3-positions of the molecule, are all preferably prepared by first acetylating the 1-position of the starting 2-indolinone compound and then effecting the desired alkylation at the 3,3-positions by means of reaction with an appropriately-substituted aralkyl halide, such as 3,4-dichlorobenzyl chloride, followed by deacetylation to afford the desired 3,3-disubstituted-2-indolinone intermediate (see Preparations O, U and X). 3-Substituted 2-indolinones of structural formula IV are also prepared in a similar manner by simply substituting an appropriate $\alpha,\alpha'$-dihalo-o-xylene for the aralkyl-halide in this sequence of reactions. (see Preparations O, Q, R, S, V and W). Lastly, 3-substituted 2-indolinones of structural formula III where the 3-substituent is the disubstituted grouping $R_4$ and $R_5$ and the disubstitution at the 3,3-positions of the molecule is unsymmetrical, are best prepared by first condensing the starting 2-indolinone compound with the appropriate aromatic or heteroaromatic aldehyde or ketone followed by subsequent catalytic reduction to the corresponding 3-monosubstituted-2-indolinone and then acetylation at the 1-position, alkylation at the 3-position (with an appropriate alkyl halide such as methyl iodide) and deacetylation at the 1-position to ultimately afford the desired 3,3-disubstituted-2-indolinone intermediate (see Preparations, N, P, T and Y).

The 2,3-dihydro-2-oxo-indoles (i.e., 2-indolinones) required as the ultimate starting materials for preparing all the compounds of this invention via the previously described reaction schemes are, for the most part, known compounds and are either readily available commercially like 2,3-dihydro-2-oxo-indole (oxindole) and 5-chloro-oxindole, or else they can easily be synthesized by those skilled in the art from common organic chemicals by using conventional methods of organic synthesis (e.g., see literature references to 6-fluoro-oxindole, 5,6-dimethoxyoxindole and 6-methoxyoxindole in Preparations C-E).

The chemical bases which are used as reagents in this invention to prepare the aforementioned pharmaceutically acceptable base salts are those which form non-toxic base salts with the herein described 3-substituted 2-oxo-indoline-1-alkanoic acid compounds such as 3-(3,4-dichlorobenzyl)-2-oxo-indoline-1-acetic acid, for example. These particular non-toxic base salts include those derived from such pharmacologically acceptable cations as sodium, potassium, calcium and magnesium, etc. These salts can easily be prepared by simply treating the aforementioned 3-substituted 2-oxo-indoline-1-alkanoic acid compounds with an aqueous solution of the desired pharmacologically acceptable cation, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

As previously indicated, the 3-substituted 2-oxoindoline-1-alkanoic acid compounds of this invention are readily adapted to therapeutic use as aldose reductase inhibitors for the control of chronic diabetic complications, in view of their ability to reduce lens sorbitol levels in diabetic subjects to a statistically significant degree. For instance, 3-(3,4-dichlorobenzyl)-2-oxoindoline-1-acetic acid, a typical and preferred agent of the present invention, has been found to inhibit the formation of sorbitol levels in diabetic rats to a significantly high degree when given by the oral route of administration at dose levels ranging from 0.75 mg./kg. to 20 mg./kg. Furthermore, the herein described compounds of this invention can be administered by either the oral or parenteral routes of administration. In general, these compounds are ordinarily administered in dosages ranging from about 0.15 mg. to about 15 mg. per kg. of body weight per day, although variations will necessarily occur depending upon the weight and condition of the subject being treated and the particular route of administration chosen.

These compounds may be administered either alone or in combination with pharmaceutically acceptable carriers by either of the routes previously indicated, and such administration can be carried out in either single or multiple dosages. More particularly, the compounds of this invention can be administered in a wide variety of different dosage forms, i.e., they may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents. In general, the compounds of the invention will be present in such dosage forms at concentration levels ranging from about 0.5% to about 90% by weight of the total composition to provide the desired unit dosage.

For oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes, and if so desired, emulsifying and/or suspending agents as well, together with such diluents as water, ethanol, propylene glycol, glycerin and various combinations thereof.

For parenteral administration, solutions of these 3-substituted 2-oxo-indoline-1-alkanoic acids in sesame or peanut oil or in aqueous propylene glycol or N,N-dimethylformamide may be employed, as well as sterile aqueous solutions of the corresponding water-soluble, alkali metal or alkaline-earth metal salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection. In this connection, the sterile aqueous media employed are all readily obtainable by standard techniques well-known to those skilled in the art. Additionally, it is also possible to administer the aforesaid oxindole-1-alkanoic acid compounds topically via an appropriate ophthalmic solution applied dropwise to the eye.

The activity of the compounds of the present invention, as agents for the control of chronic diabetic complications, is determined by their ability to successfully pass one or more of the following standard biological or pharmacological tests, viz., (1) measuring their ability to inhibit the enzyme activity of isolated aldose reductase; (2) measuring their ability to reduce or inhibit sorbitol accumulation in the sciatic nerve of acutely streptozotocinized (i.e., diabetic) rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats, and (5) measuring their ability to delay cataract formation and reduce the severity of lens opacities in chronic galactosemic rats.

PREPARATION A

To a well-stirred suspension consisting of 12.5 g. (0.091 mole) of 2,3-dihydro-2-oxo-indole(oxindole) and 16.0 g. (0.091 mole) of 3,4-dichlorobenzaldehyde in 30 ml. of methanol, there were carefully added 7.6 ml. of pyrrolidine in a dropwise manner (the reaction is exothermic). The resulting reaction mixture was then heated on a steam bath for a period of 15 minutes, followed by cooling to room temperature ($\sim 20°$ C.). The precipitated orange product was recovered by means of filtration, washed with 30 ml. of cold methanol and dried in vacuo to constant weight to ultimately afford 21.4 g. (81%) of pure 3-(3,4-dichlorobenzylidene)-2-indolinone, m.p. 183°–186° C.; mass spectrum, m/e 291/289.

Anal. Calcd. for $C_{15}H_{19}NOCl_2$: C,62.09; H, 3.13; N, 4.83. Found: C, 62.16; H, 3.28; N, 4.85.

PREPARATION B

The procedure described in Preparation A was repeated except that 5-chloro-oxindole was the starting material employed in place of oxindole, using the same molar proportions as before. In this particular case, the corresponding final product obtained was 5-chloro-3-(3,4-dichlorobenzylidene)-2-indolinone, m.p. 272°–275° C. after recrystallization from methanol. The yield of pure product was 82% of the theoretical value.

PREPARATION C

The procedure described in Preparation A was repeated except that 6-fluoro-oxindole [M. Protiva et al., *Collect. Czech. Chem. Commun.*, Vol. 44, p. 2108 (1979)]was the starting material employed in place of oxindole, using the same molar proportions as before. In this particular case, the corresponding final product obtained was 3-(3,4-dichlorobenzylidene)-6-fluoro-2-indolinone, isolated as the quarter-hydrate, m.p. 217°–220° C. after recrystallization from methanol. The yield of pure product was 84% of the theoretical value.

PREPARATION D

The procedure described in Preparation A was repeated except that 5,6-dimethoxyoxindole [G. Walker, *J. Am. Chem. Soc.*, Vol. 77, p. 3844 (1955)]was the starting material employed in place of oxindole, using the same molar proportions as before. In this particular case, the corresponding final product obtained was 3-(3,4-dichlorobenzylidene)-5,6-dimethoxy-2-indolinone, m.p. 248°–250° C. (decomp.) after recrystallization from methanol. The yield of pure product was 88% of the theoretical value.

PREPARATION E

The procedure described in Preparation A was repeated except that 6-methoxyoxindole [A. Beckett et al., *Tetrahedron*, Vol. 24, p. 6093 (1968)]was the starting material employed in place of oxindole using the same molar proportions as before. In this particular case, the corresponding final product obtained was 3-(3,4-dichlorobenzylidene)-6-methoxy-2-indolinone, m.p. 189°–191° C. after recrystallization from methanol. The yield of pure product was 85% of the theoretical value.

PREPARATION F

The procedure described in Preparation A was repeated except that 3,4-dichloro-acetophenone was the starting material employed in place of 3,4-dichlorobenzaldehyde, using the same molar proportions as before. In this particular case, the corresponding final product obtained was 3-(3,4-dichloro-α-methylbenzylidene)-2-indolinone, m.p. 233°–235° C. after recrystallization from methanol. The yield of pure product was 82% of the theoretical value.

PREPARATION G

A stirred mixture consisting of 480 mg. (0.01 mole) of pentane-washed sodium hydride dispersed in mineral oil (50% oil dispersion) and 40 ml. of dry N,N-dimethylformamide was treated with 2.9 g. (0.097 mole) of 3-(3,4-dichlorobenzylidene)-2-indolinone (the product of Preparation A) under a dry nitrogen atmosphere to give a brown homogeneous solution within a period of 20 minutes. To the stirred brown solution, there were then added 2.29 g. (0.01 mole) of benzyl bromoacetate at room temperature and the resulting reaction mixture was thereafter stirred at 25° C. for a period of 48 hours. Upon completion of this step, the final organic solution thus obtained was diluted with water (~100 ml.) and then extracted with five-100 ml. portions of chloroform. The combined organic extracts were thereafter washed with water and saturated aqueous sodium chloride, followed by drying over anhydrous magnesium sulfate. After removal of the drying agent by means of filtration and the solvent by means of evaporation under reduced pressure, there was ultimately obtained a yellow solid (yield, 4.75 g.) as the residue. The latter material was subsequently recrystallized from chloroform to afford 2.28 g. (52%) of pure cis-3-(3,4-dichlorobenzylidene)-2-oxoindoline-1-acetic acid benzyl ester, isolated as the semihydrate, m.p. 190°–192° C.; mass spectrum, m/e 439/437.

Anal. Calcd. for $C_{24}H_{17}NO_3Cl_2O.5H_2O$: C, 64.44; H, 4.06; N, 3.66. Found: C, 64.17; H, 4.29; N, 3.13.

PREPARATION H

The procedure described in Preparation G was repeated except that 5-chloro-3-(3,4-dichlorobenzylidene)-2-indolinone (the product of Preparation B) was the starting material employed in place of 3-(3,4-dichlorobenzylidene)-2-indolinone, using the same molar portions as before. In this particular case, the corresponding final product obtained was 5-chloro-3-(3,4-dichlorobenzylidene)-2-oxo-indoline-1-acetic acid benzyl ester, isolated as the quarter-hydrate, m.p. 196°–198° C. after recrystallization from ethyl acetate. The yield of pure product was 82% of the theoretical value.

PREPARATION I

The procedure described in Preparation G was repeated except that 3-(3,4-dichlorobenzylidene)-6-fluoro-2-indolinone (the product of Preparation C) was the starting material employed in place of 3-(3,4-dichlorobenzylidene)-2-indolinone, using the same molar proportions as before. In this particular case, the corresponding final product obtained was 3-(3,4-dichlorobenzylidene)-6-fluoro-2-oxo-indoline-1-acetic acid benzyl ester, isolated as the semihydrate, m.p. 198°–200° C. after recrystallization from N,N-dimethylformamide/water. The yield of pure product was 78% of the theoretical value.

PREPARATION J

The procedure described in Preparation G was repeated except that 3-(3,4-dichlorobenzylidene)-5,6-dimethoxy-2-indolinone (the product of Preparation D) was the starting material employed in place of 3-(3,4-dichlorobenzylidene)-2-indolinone, using the same molar proportions as before. In this particular case, the corresponding final product obtained was 3-(3,4-dichlorobenzylidene)-5,6-dimethoxy-2-oxo-indoline-1-acetic acid benzyl ester, m.p. 213°–215° C. after recrystallization from N,N-dimethylformamide/water. The yield of pure product was 93% of the theoretical value.

PREPARATION K

The procedure described in Preparation G was repeated except that 3-(3,4-dichlorobenzylidene)-6-methoxy-2-indolinone (the product of Preparation E) was the starting material employed in place of 3-(3,4-dichlorobenzylidene)-2-indolinone, using the same molar proportions as before. In this particular case, the corresponding final product obtained was 3-(3,4-dichlorobenzylidene)-6-methoxy-2-oxo-indoline-1-acetic acid benzyl ester, m.p. 146°–148° C. (decomp.) after recrystallization from N,N-dimethylformamide/water. The yield of pure product was 83% of the theoretical value.

PREPARATION L

The procedure described in Preparation G was repeated except that benzyl 2-chloropropionate was the reagent employed in place of benzyl bromoacetate, using the same molar proportions as before. In this particular case, the corresponding final product obtained was 3-(3,4-dichlorobenzylidene)-2-oxo-indoline-1-(α-methyl)acetic acid benzyl ester (in the form of a gum). The yield of pure product was 13% of the theoretical value.

PREPARATION M

The procedure described in Preparation G was repeated except that 3-(3,4-dichloro-α-methylbenzylidene)-2-indolinone (the product of Preparation F) was the starting material employed in place of 3-(3,4-dichlorobenzylidene)-2-indolinone, using the same molar proportions as before. In this particular case, the corresponding final product obtained was 3-(3,4-dichloro-α-methylbenzylidene)-2-oxo-indoline-1-acetic acid benzyl ester, m.p. 120°–122° C. after recrystallization from methylene chloride. The yield of pure product was 18% of the theoretical value.

PREPARATION N

A suspension consisting of 5.0 g. (0.0164 mole) of 3-(3,4-dichloro-α-methylbenzylidene)-2-indolinone (the product of Preparation M) and 1.0 g. of 5% palladium-on-carbon catalyst in 100 ml of ethanol and 100 ml. of ethyl acetate was hydrogenated on a Parr shaker at 50 p.s.i. pressure for a period of four hours (20 p.s.i. hydrogen uptake was observed). The reaction mixture was then filtered through Celite (diatomaceous earth) to remove the catalyst, and the resulting filtrate subsequently concentrated in vacuo to give a red-orange gum that slowly crystallized on standing for a period of approximately 16 hours (overnight). In this way, there were readily obtained 5.2 g. of 3-(3,4-dichloro -α-methylbenzyl)-2-indolinone, m.p. 127°–129° C. The product was further characterized by means of mass spectroscopy, nuclear magnetic resonance data and thin layer chromatography.

PREPARATION O

N-Acetyl-2-indolinone was prepared according to the procedure described by G. Walker in the *Journal of the American Chemical Society*, Vol. 77, p. 3844 (1955). This involved refluxing a mixture of 50 g. (0.376 mole) of oxindole in 500 ml. of acetic anhydride for five hours, then cooling and filtering the resulting crystalline product. In this way, there were eventually obtained 64.5 g. (98%) of pure N-acetyl-2-indolinone, m.p. 124°–126° C. (literature m.p. 127° C., according to the aforesaid reference).

PREPARATION P

The procedure described in Preparation O was repeated except that 3-(3,4-dichloro-α-methylbenzyl)-2-indolinone (the product of Preparation N) was the starting material employed in place of oxindole, using the same weight-volume proportions of reactant and reagent as before. This involved refluxing a mixture of 5.2 g. (0.0164 mole) of the indolinone in 100 ml. (1.06 mole) of acetic anhydride for a period of five hours, followed by cooling to room temperature (~20° C.) and subsequent evaporation of the solution under reduced pressure to afford a dark red-brown oil. The latter material was then dissolved in 150 ml. of ethyl acetate, washed once with water, once with saturated aqueous sodium bicarbonate solution and once with brine, followed by drying over anhydrous magnesium sulfate. After removal of the drying agent by means of filtration and the solvent by means of evaporation under reduced pressure, there was obtained 5.5 g. (97%) of pure N-acetyl-3-(3,4-dichloro-α-methylbenzyl)-2-indolinone in the form of an orange-red oil as the residue. The pure product was characterized by means of mass spectroscopy and nuclear magnetic resonance data.

PREPARATION Q

A mixture consisting of 5.0 g. (0.0306 mole) of N-acetyl-2-indolinone (the product of Preparation (O) and 9.8 g. (0.0708 mole) of potassium carbonate in 100 ml. of N,N-dimethylformamide was stirred under a dry nitrogen atmosphere at 25° C., while 8.4 g. (0.0306 mole) of α,α'-dibromo-o-xylene (96% pure; available from the Aldrich Chemical Company, Inc. of Milwaukee, Wisconsin) was slowly added thereto. After allowing the reaction mixture to stand for four days at 25° C., the resulting mixture containing the orange solid product was poured over 300 ml. of ice water and stirred for 30 minutes, followed by suction filtration. In this way, there were eventually obtained 7.4 g. (87%) of pure 1'-acetyl-1,2-dihydro-spiro-inden[2,3']-indolin-2'-one semihydrate, m.p. 159° C. (decomp.) after first washing with water and air drying to constant weight. Recrystallization of the latter material from aqueous N,N-dimethformamide did not change the value of the melting point. The mass spectrum was m/e 277.

Anal. Calcd. for $C_{18}H_{15}NO_2 \cdot 0.5H_2O$: C, 75.50; H, 5.63; N, 4.89. Found: C, 75.77; H, 5.54; N, 4.92.

PREPARATION R

To 25 g. (0.178mole) of 4-chloro-o-xylene heated to 130° C. and illuminated with a 100 Watt incandescent lamp, there were added with stirring 19.6 ml. (0.382 mole) of bromine in a dropwise manner over a period of 35 minutes. Upon completion of this step, the resulting reaction mixture was stirred at 130° C. for an additional 1.5 hours and then cooled to 25° C. and allowed to stir overnight (~16 hours). At this point, the excess hydrogen bromide and bromine were removed in vacuo and the residual product was fractionally distilled as a pale yellow oil to afford 23.1 g. (44%) of pure 1,2-bis(bromomethyl)-4-chlorobenzene, b.p 128°–137° C./0.6 mm. Hg; mass spectrum, m/e 296, 298,.300.

PREPARATION S

The procedure described in Preparation Q was repeated except that 1,2-bis(bromomethyl)-4-chlorobenzene (the product of Preparation R) was the alkylating agent employed in place of α,α'-dibromo-o-xylene, using the same molar proportions as before. In the particular case, the corresponding final product obtained was 1'-acetyl-5(6)-chloro-1,2-dihydro-spiroinden[2,3-']indolin-2'-one, m.p. 108°–110° C. after recrystallization from aqueous N,N-dimethylformamide. The yield of pure product was 57% of the theoretical value.

PREPARATION T

A stirred mixture consisting of 760 mg. (0.0158 mole) of pentane-washed sodium hydride (50% oil dispersion) and 100 ml. of dry N,N-dimethylformamide was treated under a dry nitrogen atmosphere with 5.5 g. (0.0158 mole) of N-acetyl-3-(3,4-dichloro-α-methylbenzyl)-2-indolinone (the product of Preparation P) dissolved in 50 ml. of dry N,N-dimethylformamide. The latter solution was added over the course of a two-minute period and when the addition was complete, the resulting mixture was stirred at room temperature (~20° C.) for a period of 30 minutes to give a dark brown solution. At this point, 1.0 ml. (0.016 mole) of methyl iodide was added and the final reaction mixture was stirred at room temperature for a period of 18 hours. Upon completion of this step, the resulting organic solution was poured onto 200 ml. of ice/water and stirred for a period of one hour, followed by extraction with diethyl ether. The ethereal extract was thereafter washed with water and brine, and finally dried over anhydrous magnesium sulfate. After removal of the drying agent by means of filtration and the solvent by means of evaporation under reduced pressure, there was obtained a yellow residual oil which consisted of 4.05 g. (71%) of pure 1-acetyl-3-(3,4-dichloro-α-methylbenzyl)-3-methyl-2-indolinone. The pure product was characterized by means of mass spectroscopy, nuclear magnetic resonance and thin layer chromatography.

PREPARATION U

A mixture consisting of 5.0 g. (0.0306 mole) of N-acetyl-2-indolinone (the product of Preparation O), 9.8 g. (0.0708 mole) of potassium carbonate and 11.6 g. (0.070 mole) of potassium iodide in 80 ml. of N,N-dimethylformamide was stirred under a dry nitrogen atmosphere at room temperature (~20° C.), while a solution consisting of 8.9 ml. (0.0643 mole) of 3,4-dichlorobenzyl chloride dissolved in 20 ml. of N,N-dimethylformamide was slowly added thereto. The resulting reaction mixture was then stirred at room temperature for a period of 72 hours and finally partitioned between water and diethyl ether. The aqueous layer was then extracted twice with diethyl ether, and the combined organic layers were subsequently washed once with water and once with brine, followed by drying over anhydrous magnesium sulfate. After removal of the drying agent by means of filtration and the solvent by means of evaporation under reduced pressure, there was obtained a pale pink solid as the residue. Recrystallization of the latter material from aqueous N,N-dimethylformamide then gave 5.75 g. (38%) of pure 1-acetyl-3,3-di(3,4-dichlorobenzyl)-2-indolinone monohydrate, m.p. 177°–179° C. after first drying to constant weight in vacuo for a period of approximately 16 hours (i.e., overnight). The pure product was further characterized by means of mass spectroscopy, nuclear magnetic resonance data and thin layer chromatography, in addition to elemental analysis.

Anal. Calcd. for $C_{24}H_{17}NO_2Cl_4 \cdot H_2O$: C, 56.38; H, 3.75; N, 2.74. Found: C, 56.43; H, 3.52; N, 2.80.

PREPARATION V

A mixture consisting of 7.4 g. (0.0267 mole) of 1'-acetyl-1,2-dihydro-spiro-inden[2,3']indolin-2'-one semihydrate (the product of Preparation Q) in 170 ml. of 4% aqueous sodium hydroxide and 170 ml. of absolute methanol was stirred and heated on a steam bath for a period of 30 minutes. Upon completion of this step, the resulting solution was cooled to 25° C. and then acidified to pH 2 with concentrated hydrochloric acid. After removal of excess methanol by means of evaporation under reduced pressure, the resulting solids were filtered, washed with water and dried in vacuo to constant weight to ultimately afford 5.65 g. (90%) of pure 1,2-dihydro-spiro-inden[2,3']indolin-2'-one semihydrate, m.p. 186°–189° C. Recrystallization of the latter material from aqueous methanol did not change value of the melting point. The mass spectrum was m/e 235.

Anal. Calcd. for $C_{16}H_{13}NO.0.5H_2O$: C, 78.66; H, 5.78; N, 5.74. Found: C, 78.96; H, 5.64; N, 5.74.

PREPARATION W

The procedure described in Preparation V was repeated except that 1'-acetyl-5(6)-chloro-1,2-dihydrospiro-inden[2,3']indolin-2'-one (the product of Preparation S) was the starting material employed in place of 1'-acetyl-1,2-dihydro-spiro-inden[2,3']indolin-2-one semihydrate, using the same molar proportions as before. In this particular case, the corresponding final product obtained was 5(6)-chloro-1,2-dihydrospiro-inden[2,3']indolin-2'-one, m.p. 160°–163° C. (decomp.). The yield of pure product was 61% of the theoretical value.

PREPARATION X

The procedure described in Preparation V was repeated except that 1-acetyl-3,3-di(3,4-dichlorobenzyl)-2-indolinone monohydrate (the product of Preparation U) was the starting material employed in place of 1'-acetyl-1,2-dihydro-spiro-inden[2,3']-indolin-2'-one, using the same molar proportions as before. In this particular case, the corresponding final product obtained was 3,3-di(3,4-dichlorobenzyl)-2-indolinone, m.p. 165°–170° C. after recrystallization from aqueous methanol. The yield of pure product was 87% of the theoretical value.

PREPARATION Y

A mixture consisting of 4.0 g. (0.011 mole) of 1-acetyl-3-(3,4-dichloro-α-methylbenzyl)-3-methyl-2-indolinone (the product of Preparation T) in 70 ml. of 4% aqueous sodium hydroxide and 70 ml. of absolute methanol was stirred and heated on a steam bath for a period of one hour. At this point, an additional 40 ml. of 4% aqueous sodium hydroxide was added to the mixture, followed by continued refluxing on the steam bath for a further period of three hours. Upon completion of this step, the resulting reaction solution was stirred at room temperature (~20° C.) for approximately 18 hours (overnight) and then acidified to pH 1.0 with 6N hydrochloric acid. Extraction of the product was next accomplished with three-100 ml. portions of methylene chloride, and the combined organic layers were subsequently washed with water and brine, followed by drying over anhydrous magnesium sulfate. After removal of the drying agent by means of filtration and the solvent by means of evaporation under reduced pressure, there were obtained 3.41 g. (97%) of pure 3-(3,4-dichloro-α-methylbenzyl)-3-methyl-2-indolinone in the form of a yellow gum. The pure product was characterized by means of mass spectroscopy, nuclear magnetic resonance data and thin layer chromatography.

PREPARATION Z

The procedure described in Preparation G was repeated except that 1,2-dihydro-indene[2,3']indolin-2'-one semihydrate (the product of Preparation V) was the starting material employed in place of 3-(3,4-dichlorobenzylidene)-2-indolinone, using the same molar proportions as before. In this particular case, the corresponding final product obtained was 1,2-dihydrospiro-inden[2,3']indolin-2'-one-1'-acetic acid benzyl ester semihydrate, m.p. 141°–143° C. after recrystallization from aqueous N,N-dimethylformamide. The yield of pure product was 93% of the theoretical value.

PREPARATION AA

The procedure described in Preparation G was repeated except that 5(6)-chloro-1,2-dihydro-spiroinden[2,3']indolin-2'-one (the product of Preparation W) was the starting material employed in place of 3-(3,4-dichlorobenzylidene)-2-indolinone, using the same molar proportions as before. In this particular case, the corresponding final product obtained was 5(6)-chloro-1,2-dihydro-spiro-inden[2,3']indolin-2'-one-1'-acetic acid benzyl ester, m.p. 136°–140° C. after recrystallization from chloroform. The yield of pure product was 48% of the theoretical value.

PREPARATION BB

The procedure described in Preparation G was repeated except that 3,3-di(3,4-dichlorobenzyl)-2-indolinone (the product of Preparation X) was the starting material employed in place of 3-(3,4-dichlorobenzylidene)-2-indolinone, using the same molar proportions as before. In this particular case, the corresponding final product obtained was 3,3-di(3,4-dichlorobenzyl)-2-oxo-indoline-1-acetic acid benzyl ester (obtained as an oil). The yield of pure product was 48% of the theoretical value.

PREPARATION CC

The procedure described in Preparation G was repeated except that 3-(3,4-dichloro-α-methylbenzyl)-3-methyl-2-indolinone (the product of Preparation Y) was the starting material employed in place of 3-(3,4-dichlorobenzylidene)-2-indolinone, using the same molar proportions as before. In this particular case, the corresponding final product obtained was 3-(3,4-dichloro-α-methylbenzyl)-3-methyl-2-oxo-indoline-1-acetic acid benzyl ester (obtained as an oil). The yield of pure product was 79% of the theoretical value.

EXAMPLE 1

A suspension consisting of 2.28 g. (0.0052 mole) of cis-3-(3,4-dichlorobenzylidene)-2-oxo-indoline-1-acetic acid benzyl ester as the semihydrate (the product of Preparation G) and 1.0 g. of 5% palladium-on-carbon catalyst in 50 ml. of ethyl acetate containing 2 ml. of glacial acetic acid was hydrogenated at atmospheric pressure until the uptake of hydrogen gas ceased (~3 hours). Thin layer chromatography analysis, using chloroform/methanol (9:1 by volume) as the eluant, showed no benzyl ester present at this point and revealed a single product at $R_f=0.50$. The reaction solution was then filtered through Celite (diatomaceous earth) to remove the catalyst, and the resulting filtrate was subsequently concentrated in vacuo to a pale yellow foam. Recrystallization of the latter material from aqueous ethanol then gave a white solid product consisting of 1.325 g. (73%) of pure 3-(3,4-dichlorobenzyl)-2-oxo-indoline-1-acetic acid, m.p. 168°-171° C.; mass spectrum, m/e 351/349.

Anal. Calcd. for $C_{17}H_{13}NO_3Cl_2$: C, 58.30; H, 3.74; N, 4.00. Found: C, 58.54; H, 3.88; N, 3.91.

EXAMPLE 2

The hydrogenolysis procedure described in Example 1 was repeated except that 5-chloro-3-(3,4-dichlorobenzylidene)-2-oxo-indoline-1-acetic acid benzyl ester as the quarter-hydrate (the product of Preparation H) was the starting material employed in place of the semihydrate of cis-3-(3,4-dichlorobenzylidene)-2-oxoindoline-1-acetic acid benzyl ester. In this particular case, the corresponding final product obtained was 5-chloro-3-(3,4-dichlorobenzyl)-2-oxo-indoline-1-acetic acid isolated as the dicyclohexylamine salt, m.p. 148°-150° C. after recrystallization from ethanol/diethyl ether. The yield of pure product was 18% of the theoretical value.

EXAMPLE 3

The hydrogenolysis procedure described in Example 1 was repeated except that 3-(3,4-dichlorobenzylidene)-6-fluoro-2-oxo-indoline-1-acetic acid benzyl ester as the quarter-hydrate (the product of Preparation I) was the starting material employed in place of the semihydrate of cis-3-(3,4-dichloro-benzylidene)-2-oxoindoline-1-acetic acid benzyl ester. In this particular case, the corresponding final product obtained was 3-(3,4-dichlorobenzyl)-6-fluoro-2-oxo-indoline-1-acetic acid, isolated as the dicyclohexylamine salt, m.p. 157°-160° C. (decomp.) after recrystallization from diethyl ether/pentane. The yield of pure product was 28% of the theoretical value.

EXAMPLE 4

The hydrogenolysis procedure described in Example 1 was repeated except that 3-(3,4-dichlorobenzylidene)-5,6-dimethoxy-2-oxo-indoline-1-acetic acid benzyl ester (the product of Preparation J) was the starting material employed in place of the semihydrate of cis-3-(3,4-dichlorobenzylidene)-2-oxo-indoline-1-acetic acid benzyl ester. In this particular case, the corresponding final product obtained was 3-(3,4-dichlorobenzyl)-5,6-dimethoxy-2-oxo-indoline-1-acetic acid, isolated as the dicyclohexylamine salt, m.p. 222°-223° C. (decomp.) after recrystallization from diethyl ether. The yield of pure product was 17% of the theoretical value.

EXAMPLE 5

The hydrogenolysis procedure described in Example 1 was repeated except that 3-(3,4-dichlorobenzylidene)-6-methoxy-2-oxo-indoline-1-acetic acid benzyl ester (the product of Preparation K) was the starting material employed in place of the semihydrate of cis-3-(3,4-dichlorobenzylidene)-2-oxo-indoline-1-acetic acid benzyl ester. In this particular case, the corresponding final product obtained was 3-(3,4-dichlorobenzyl)-6-methoxy-2-oxo-indoline-1-acetic acid, isolated as the dicyclohexylamine salt, m.p. 182°-183° C. after recrystallization from diethyl ether. The yield of pure product was 81% of the theoretical value.

EXAMPLE 6

The hydrogenolysis procedure described in Example 1 was repeated except that 3-(3,4-dichlorobenzylidene)-2-oxo-indoline-1-($\alpha$-methyl)acetic acid benzyl ester (the product of Preparation L) was the starting material employed in place of the semihydrate of cis-3-(3,4-dichlorobenzylidene)-2-oxo-indoline-1-acetic acid benzyl ester. In this particular case, the corresponding final product obtained was 3-(3,4-dichlorobenzyl)-2-oxo-indoline-1-($\alpha$-methyl)acetic acid, isolated as the semihydrate of the dicyclohexylamine salt, m.p. 94°-96° C. (decomp.) The yield of pure product was 57% of the theoretical value.

EXAMPLE 7

The hydrogenolysis procedure described in Example 1 was repeated except that 3-(3,4-dichloro-$\alpha$-methylbenzylidene)-2-oxo-indoline-1-acetic acid benzyl ester (the product of Preparation M) was the starting material employed in place of the semihydrate of cis-3-(3,4-dichlorobenzylidene)-2-oxo-indoline-1-acetic acid benzyl ester. In this particular case, the corresponding final product obtained was 3-(3,4-dichloro-$\alpha$-methylbenzyl)-2-oxo-indoline-1-acetic acid, m.p. 175°-177° C. (decomp.) after recrystallization from aqueous ethanol. The yield of pure product was 50% of the theoretical value.

EXAMPLE 8

The hydrogenolysis procedure described in Example 1 was repeated except that the semihydrate of 1,2-dihydro-spiro-inden[2,3']indolin-2'-one-1'-acetic acid benzyl ester (the product of Preparation Z) was the starting material employed in place of the semihydrate of cis-3-(3,4-dichlorobenzylidene)-2-oxo-indoline-1-acetic acid benzyl ester. In this particular case, the corresponding final product obtained was 1,2-dihydrospiro-inden[2,3-']indolin-2'-one-1'-acetic acid, isolated as the dicyclohexylamine salt, m.p. 185°-187° C. after recrystallization from ethanol/diethyl ether. The yield of pure product was 13% of the theoretical value.

EXAMPLE 9

The hydrogenolysis procedure described in Example I was repeated except that 5(6)-chloro-1,2-dihydrospiro-inden[2,3']indolin-2'-one-1'-acetic acid benzyl ester (product of Preparation AA) was the starting material employed in place of the semihydrate of cis-3-(3,4-dichlorobenzylidene-2-oxo-indoline-1-acetic acid benzyl ester. In this particular case, the corresponding final product obtained was 5(6)-chloro-1,2-dihydro-spiro-inden[2,3']indolin-2'-one-1'-acetic acid, isolated as the dicyclohexylamine salt, m.p. 135°-136° C. (decomp.) after recrystallization from ethanol/pentane. The yield of pure product was 89% of the theoretical value.

EXAMPLE 10

The hydrogenolysis procedure described in Example 1 was repeated except that 3,4-di(3,4-dichlorobenzyl)-2-oxo-indoline-1-acetic acid benzyl ester (the product of Preparation BB) was the starting material employed in place of the semihydrate of cis-3-(3,4-dichlorobenzylidene)-2-oxo-indoline-1-acetic acid benzyl ester. In this particular case, the corresponding final product obtained was 3,3-di(3,4-dichlorobenzyl)-2-oxo-indoline-1-acetic acid, isolated as the dicyclohexylamine salt, m.p. 185°-186° C. after recrystallization from diethylether/pentane. The yield of pure product was 65% of the theoretical value.

EXAMPLE 11

The hydrogenolysis procedure described in Example 1 was repeated except that 3-(3,4-dichloro-$\alpha$-methylbenzyl)-3-methyl-2-oxo-indoline-1-acetic acid benzyl ester (the product of Preparation CC) was the starting material employed in place of cis-3-(3,4-dichlorobenzylidene)-2-oxo-indoline-1-acetic acid benzyl ester. In this particular case, the corresponding final product obtained was 3-(3,4-dichloro-α-methylbenzyl)-3-methyl-2-oxo-indoline-1-acetic acid, isolated as the dicyclohexylamine salt, m.p. 151°–153° C. after recrystallization from diethyl ether. The yield of pure product was 72% of the theoretical value.

EXAMPLE 12

A solution consisting of 1.8 g. (0.0473 mole) of 3-(3,4-dichlorobenzyl)-6-methoxy-2-oxo-indoline-1-acetic acid as the dicyclohexylamine salt (the product of Example 5) dissolved in 60 ml. of methylene chloride was cooled to 0° C. while under a nitrogen atmosphere and treated with 9.5 ml. (0.095 mole) of 1M boron tribromide in methylene chloride, which was added in a dropwise manner over a period of 1.5 minutes. Upon completion of this step, the resulting reaction mixture was stirred for a period of 15 minutes and then allowed to warm to 25° C. over a period of one hour to give a clear red solution. At this point, another 10 ml. portion of 1M boron tribromide in methylene chloride was added to the mixture, which was then stirred overnight (~18 hours) at 25° C. and subsequently poured over 100 ml. of ice water. The product thus obtained was then extracted from the aqueous layer, first with methylene chloride and then with ethyl acetate, and the combined organic layers were subsequently washed once with water and once with brine, followed by drying over anhydrous magnesium sulfate. After removal of the drying agent by means of filtration and the solvent by means of evaporation under reduced pressure, there was obtained a viscous oil (yield, 1.7 g.) as the residue. The latter material was subsequently dissolved in 150 ml. of anhydrous diethyl ether and treated with 2.4 ml. (~2.5 equivalents) of dicyclohexylamine and then allowed to crystallize. In this way, there was readily obtained the corresponding crystalline dicyclohexylamine salt, which was thereafter recovered by means of filtration, washed with diethyl ether and pentane, and then dried in vacuo to constant weight to ultimately afford 1.7 g. (65%) of pure 3-(3,4-dichlorobenzyl)-6-hydroxy-2-oxo-indoline-1-acetic acid (as the dicyclohexylamine salt), m.p. 141°–144° C. (decomp.). Recrystallization of the latter material from diethyl ether did not raise the melting point.

EXAMPLE 13

The following oxindole-1-alkanoic acid final products of Examples 1–12, respectively, were tested at a concentration level of $10^{-5}$M for their ability to reduce or inhibit aldose reductase enzyme activity via the procedure of S. Hayman et al., as described in the *Journal of Biological Chemistry*, vol. 240, p. 877 (1965) and as modified by K. Senstanj et al. in U.S. Pat. No. 3,821,383. In every case, the substrate employed was partially purified aldose reductase enzyme obtained from human placenta. The results obtained with each compound are expressed below in terms of their percent inhibition of enzyme activity (%) with respect to the particular concentration level chosen ($10^{-5}$M):

| Compound | % Inhibition at $10^{-5}$M |
|---|---|
| Product of Example 1 | 92 |
| Product of Example 2 | 88 |
| Product of Example 3 | 68 |
| Product of Example 4 | 55 |
| Product of Example 5 | 81 |
| Product of Example 6 | 25 |
| Product of Example 7 | 94 |
| Product of Example 8 | 66 |
| Product of Example 9 | 71 |
| Product of Example 10 | 20 |
| Product of Example 11 | 72 |
| Product of Example 12 | 79 |

We claim:
1. An oxindole-1-alkanoic acid compound of the formula:

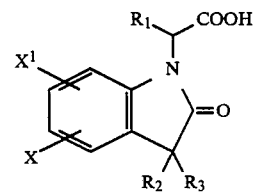

or a $C_1$-$C_6$ alkyl ester or the N,N-di(unsubstituted) primary amide derivative thereof, or a base salt of said acid with a pharmacologically acceptable cation, wherein X is hydrogen and $X^1$ is hydrogen, hydroxy, fluorine, chlorine, bromine, $C_1$-$C_4$ alkyl or $C_1$-$C_4$ alkoxy; or X and $X^1$, when taken separately, are each chlorine, $C_1$-$C_4$ alkyl or $C_1$-$C_4$ alkoxy, and when taken together are —OCH$_2$(CH$_2$)$_n$O— at the 4,5-, 5,6- or 6,7- positions of the molecule wherein n is zero or one;

$R_1$ is hydrogen or methyl;

$R_2$ is hydrogen, $C_1$-$C_4$ alkyl or phenylalkyl having up to three carbon atoms in the alkyl moiety wherein said phenylalkyl is optionally substituted with up to two chlorine substituents on the phenyl ring;

$R_3$ is naphthylmethyl, furfuryl, thenyl, benzothienylmethyl, benzoxazolylmethyl, benzothiazolylmethyl or phenylalkyl having up to three carbon atoms in the alkyl moiety wherein said phenylalkyl is optionally substituted with up to two identical or non-identical substituents on the phenyl ring, said identical substituents being fluorine, chlorine, bromine, trifluoromethyl, $C_1$-$C_4$ alkyl or $C_1$-$C_4$ alkoxy and said non-identical substituents being chlorine, methyl, methoxy or trifluoromethyl.

2. A pharmaceutical composition suitable for oral administration comprising a pharmaceutically acceptable carrier and a compound as claimed in claim 1 in an amount effective for the treatment of diabetes-associated chronic complications.

3. A method for treating a diabetic host to prevent or alleviate chronic complications arising in said host, which comprises administering to said diabetic host an effective amount of a compound as claimed in claim 1.

4. A compound as claimed in claim 1 wherein $R_3$ is phenylalkyl having up to three carbon atoms in the alkyl moiety.

5. A compound as claimed in claim 1 wherein $R_3$ is ring-substituted phenylalkyl having up to three carbon atoms in the alkyl moiety.

6. A compound as claimed in claim 5 wherein $R_3$ is ring-substituted phenylalkyl having up to two chlorine substituents on the phenyl ring.

7. A compound as claimed in claim 6 wherein X and $X^1$ are each hydrogen, $R_1$ and $R_2$ are each hydrogen and $R_3$ is 3,4-dichlorobenzyl.

8. A compound as claimed in claim 6 wherein X is hydrogen, $X^1$ is hydroxy, $R_1$ and $R_2$ are each hydrogen and $R_3$ is 3,4-dichlorobenzyl.

9. A compound as claimed in claim 8 wherein $X^1$ is hydroxy at the 6-position of the molecule.

10. A compound as claimed in claim 6 wherein X is hydrogen, $X^1$ is fluorine, $R_1$ and $R_2$ are each hydrogen and $R_3$ is 3,4-dichlorobenzyl.

11. A compound as claimed in claim 10 wherein $X^1$ is fluorine at the 6-position of the molecule.

12. A compound as claimed in claim 6 wherein X is hydrogen, $X^1$ is bromine, $R_1$ and $R_2$ are each hydrogen and $R_3$ is 3,4-dichlorobenzyl.

13. A compound as claimed in claim 6 wherein X is hydrogen, $X^1$ is chlorine, $R_1$ and $R_2$ are each hydrogen and $R_3$ is 3,4-dichlorobenzyl.

14. A compound as claimed in claim 13 wherein $X^1$ is chlorine at the 5-position of the molecule.

15. A compound as claimed in claim 6 wherein X is hydrogen, $X^1$ is $C_1$–$C_4$ alkoxy, $R^1$ and $R_2$ are each hydrogen and $R_3$ is 3,4-dichlorobenzyl.

16. A compound as claimed in claim 15 wherein $X^1$ is methoxy at the 6-position of the molecule.

17. A compound as claimed in claim 6 wherein X and $X^1$ are each hydrogen, $R_1$ is methyl, $R_2$ is hydrogen and $R_3$ is 3,4-dichlorobenzyl.

18. A compound as claimed in claim 6 wherein X and $X^1$ are each hydrogen, $R_1$ and $R_2$ are each hydrogen $R_3$ is 3,4-dichloro-α-methylbenzyl.

19. A compound as claimed in claim 6 wherein X and $X^1$ are each hydrogen, $R_1$ is hydrogen, $R_2$ is $C_1$–$C_4$ alkyl and $R_3$ is 3,4-dichloro-α-methylbenzyl.

20. A compound as claimed in claim 19 wherein $R_2$ is methyl.

21. A compound as claimed in claim 6 wherein X and $X^1$ are each hydrogen, $R_1$ is hydrogen, and $R_2$ and $R_3$ are each 3,4-dichlorobenzyl.

22. A compound as claimed in claim 6 wherein X and $X^1$, when taken separately, are each chlorine, $R_1$ and $R_2$ are each hydrogen and $R_3$ is 3,4-dichlorobenzyl.

23. A compound as claimed in claim 6 wherein X and $X^1$, when taken separately, are each $C_1$–$C_4$ alkoxy, $R_1$ and $R_2$ are each hydrogen and $R_3$ is 3,4-dichlorobenzyl.

24. A compound as claimed in claim 23 wherein X and $X^1$, when taken separately, are each methoxy at the adjacent 5,6-positions of the molecule.

25. A compound as claimed in claim 6 wherein X and $X^1$, when taken together, are —$OCH_2(CH_2)_nO$— at the adjacent 4,5-, 5,6- or 6,7-positions of the molecule and n is zero or one, $R_1$ and $R_2$ are each hydrogen and $R_3$ is 3,4-dichlorobenzyl.

26. A compound as claimed in claim 25 wherein X and $X^1$, when taken together, are methylenedioxy at the adjacent 5,6-positions of the molecule.

* * * * *